United States Patent [19]

Sytkowski et al.

[11] Patent Number: 4,590,168

[45] Date of Patent: May 20, 1986

[54] PROTEIN IMMUNOASSAYING AND PURIFICATION

[75] Inventors: Arthur J. Sytkowski, Arlington; Julia M. Sue, Brookline, both of Mass.

[73] Assignee: The Children's Medical Center Corporation, Boston, Mass.

[21] Appl. No.: 466,204

[22] Filed: Feb. 14, 1983

[51] Int. Cl.[4] .................. G01N 33/543; C07K 5/17
[52] U.S. Cl. ............................ 436/518; 436/531; 436/532; 436/512; 436/547; 436/513; 436/818; 435/810; 435/7; 422/61; 424/85; 530/806; 530/387; 530/329
[58] Field of Search ............... 436/531, 532, 512, 513, 436/818, 547; 435/810, 7; 260/112.5 R; 422/61; 424/85

[56] References Cited

U.S. PATENT DOCUMENTS

| | | | |
|---|---|---|---|
| 4,096,237 | 6/1978 | Li | 424/1 |
| 4,254,095 | 3/1981 | Fisher et al. | 436/513 |
| 4,277,437 | 7/1981 | Maggio | 436/513 |
| 4,465,624 | 8/1984 | Chiba et al. | 260/112 R |

OTHER PUBLICATIONS

Merrifield, *Biochem.* (1964) 3 (No. 9): 1385–1390.
Lerner, *Scientific American* (1983) Feb.: 66–74.
Sherwood et al. (1979) Blood 54:885.
Miyake et al. (1977) J. Biological Chem. 252:5558.
Egrie, J., Hybridoma, vol. 2, No. 1, 1983, p. 136 "Monoclonal Antibodies to the N–Terminal Region of Hyman Erythropoietin."
Weis, T. L.; et al., Characterization of a Monoclonal Antibody to Erythropoietin, Proc. Natl. Acad. Sci. U.S.A., 79 (1982), pp. 5465–5469.

*Primary Examiner*—Christine M. Nucker
*Assistant Examiner*—Stephen C. Wieder

[57] ABSTRACT

Protein immunoassay or purification using an antibody raised to an antigen comprising a polypeptide corresponding to a fragment (but not all) of the protein being assayed; the antibody is capable of binding separately both to the protein as a whole and to the polypeptide; that antibody is used to purify or (with a known concentration of the labeled polypeptide serving as a tracer) to assay the protein.

15 Claims, No Drawings

4,590,168

PROTEIN IMMUNOASSAYING AND PURIFICATION

BACKGROUND OF THE INVENTION

The invention described herein was made in the course of work under a grant or award from the Department of Health and Human Services.

The invention relates to immunoassaying for, and purification of, proteins—e.g., erythropoietin, a hormone involved in regulation of red blood cell development.

Protein immunoassays are useful, e.g., to diagnose human disease states. Abnormal levels of erythropoietin, for example, may signify many forms of anemia, certain heart and lung diseases, tumors, renal failure, and other diseases. Purified proteins and antibodies thereto are used to treat various disease states. For example, purified erythropoietin may be used to treat anemia associated with renal failure.

In protein immunoassays, a sample having an unknown concentration of the protein is mixed with a known concentration of the protein which has been labeled to form a tracer compound. The tracer and sample protein compete to bind to an antibody which has been raised to the protein. The extent to which the labeled protein binds to the antibody can be measured (either by measuring the bound or the unbound tracer) and will be inversely affected by the protein concentration in the sample, according to known relationships which may be used to derive that concentration. Thus, in the conventional immunoassay, the protein being assayed serves both as the antigen used to raise the antibody and as the labeled tracer used to determine the sample protein concentration.

Li U.S. Pat. No. 4,096,237 discloses such an immunoassay for a human protein hormone known as β-endorphin, using radioactively labeled β-endorphin as a tracer and antibodies raised to β-endorphin. Li also discloses that the above tracer and antibodies may be used to assay a related protein, such as camel β-endorphin or a specific peptide fragment thereof which "exhibited a parallel inhibition curve, but had 40% immunoreactivity as compared to the full sequence of camel β-endorphin" (2:18-20).

SUMMARY OF THE INVENTION

In one aspect, the invention features, generally, in a protein immunoassay, an antibody raised to an antigen which comprises a polypeptide corresponding to a fragment (but not all) of the protein being assayed. The antibody is capable of binding separately both to the protein as a whole and to the polypeptide; that antibody is used to assay the protein, and a known concentration of the labeled polypeptide serves as a tracer.

In another aspect, the invention features, generally, the use of the above-described antibody to purify the protein by introducing the antibody into a mixture containing the protein, separating the bound protein/antibody from the mixture, and then separating the protein from the antibody.

In preferred embodiments, the polypeptide comprises an epitope of the protein; most preferably, the protein is erythropoietin, and the polypeptide corresponds to at least a fragment of the twenty-six amino-acid sequence at the N terminus of erythropoietin.

The invention enables a readily available, reliable assay for proteins, particularly those which are available, if at all, in limited supply and purity. The use of a pure polypeptide, rather than relatively impure supplies of the entire protein, yields antibodies of greater specificity that provide more consistent assay results. Often, the polypeptide is more easily handled, stored, and synthesized and cheaper than the full protein. The invention provides similar benefits in methods of immunological purification of proteins.

Other features and advantages of the invention will be apparent from the following description of the preferred embodiments thereof, and from the claims.

DESCRIPTION OF THE PREFERRED EMBODIMENTS

We turn first to the labeled polypeptide tracer.

Tracer

The tracer may be any labeled polypeptide that includes a sequence of amino acids corresponding to a fragment of the protein of interest (i.e., the protein being assayed or purified), so long as the polypeptide is capable (either by itself or when combined with a carrier) of "raising an antibody" (i.e., stimulating an animal to produce an antibody) which will separately bind both to the protein and to the polypeptide. As used herein, the term polypeptide means any sequence of amino acids shorter than the complete protein of interest. Preferably, the fragment of the protein comprises an epitope of the protein, i.e., a portion of the protein, usually at least six amino acids long, which an antibody can recognize and bind to.

The label of the tracer is any suitable detectable entity, e.g., a radioactive element such as $^{125}I$, $^{14}C$, or $^{3}H$, a fluorescent molecule, a photometrically detectable compound, or an enzymatically detectable compound.

The polypeptide of the tracer may be synthesized by various peptide synthesis techniques known to those in the art. The polypeptide may also be derived from the protein, e.g., by using various enzymes which specifically attack the protein at pre-determined linkages.

A tracer useful for assaying the protein erythropoietin is an $^{125}I$-labeled polypeptide sequence corresponding to a fragment of the 26 amino-acid segment of the N-terminus of erythropoietin. A specific sequence that is useful in assaying for erythropoietin is as follows: H₂N-ala-pro-pro-arg-leu-ile-asn-asp-ser-arg-val-leu-glu-arg-tyr-leu-leu-glu-ala-lys-glu-ala-glu-lys-ile-thr-COOH.

The above polypeptide sequence may be synthesized chemically by techniques described in R. B. Merrifield, Biochem (1964) 3:1385 et seq, and the resulting polypeptide (PP) labeled with $^{125}I$ as follows. First, the following constituents are added to a 5 ml polystyrene test tube on ice:

(1) 1.25 mCi Na $^{125}I$ in 0.1N NaOH (25 μl);

(2) a neutralizing solution comprising 2 parts 0.1M sodium phosphate (at pH 7.5) per 1 part 0.1N HCl (75 μl); and (3) the polypeptide (2 μl of 5 mg/ml) (10 μg). To that mixture is added 60 μl of 0.5 mg/ml Chloramine-T. After 20 seconds, 60 μl of 125 mg/ml sodium metabisulfite is added. Finally, 778 μl of NaI solution (2 mg/ml in 0.1M sodium phosphate; 2 mg/ml bovine serum albumin at pH 7.5) is added.

Ten microliters of the final 1.0 ml reaction mixture is removed and the radioactivity determined by gamma scintillation spectrometry. From this, the total radioactivity in the reaction mixture is calculated according to the following equation.

Total radioactivity, mCi =

$$\frac{\text{cpm of 10 } \mu \text{ l sample 100}}{(0.813, \text{ counter efficiency})(2.2 \times 10^9 \text{ dpm/mCi})}$$

The [$^{125}$I]PP is separated from unreacted $^{125}$I by gel filtration of the reaction mixture through a 1.5×20 cm column of Bio-Gel P-4 equilibrated with 25 mM sodium phosphate, (0.15M NaCl, 2 mg/ml BSA at pH 7.5). One ml fractions are collected and the radioactivity of each determined. The [$^{125}$I]PP elutes as a single peak. The total mCi within the peak is determined and the specific activity of the [$^{125}$I]PP expressed as Ci/mmol. Using the above procedure, a specific activity of about 700 Ci/mmol is typical. The solution of [$^{125}$I]PP is divided into aliquots and frozen.

We now turn to a description of the antibody raised using the polypeptide described above.

Antibody

The antibody is raised to an antigen comprising the polypeptide described above and screened to establish its ability to bind separately to both the protein and to the polypeptide. For example, the screen for affinity to the polypeptide may involve an enzyme-linked immunosorbent assay (ELISA); the screen for affinity with the protein may be accomplished by incubating the antibody with labeled protein, after which the resulting antibody-protein complex is precipitated and subjected to gel electrophoresis. The antibody is raised by administering the polypeptide, either by itself or bound to a suitable carrier, for example a carrier protein such as bovine serum albumin (BSA), to a mammal, e.g., rabbits, and harvesting the antibody thus produced.

Antibodies useful in the erythropoietin assay are raised by immunizing New Zealand white rabbits with 50 μg of the above-described polypeptide, preferably conjugated with bovine serum albumin (8.1 mg PP per 6.7 mg BSA, or approximately 20 molecules of PP per molecule of BSA) in Freund's complete adjuvant by multiple intradermal injections. Subcutaneous booster injections are administered over several weeks.

The resulting animal sera are screened for anti-PP antibodies by an enzyme-linked immunosorbent assay (ELISA). PP (0.1 μg/ml in 50 mM NaCO$_3$) is bound to polystyrene microwells (Immulon 2, Dynatech) by adsorption. Serial dilutions of rabbit sera are incubated for 1 hour in PP-coated wells. After washing unbound antibodies, the bound anti-PP antibodies are detected using horseradish peroxidase-conjugated goat anti-rabbit IgG (Cappel Laboratories). ELISA procedures demonstrate that there are anti-PP antibodies in the rabbit sera.

To establish affinity of the antibodies for erythropoietin (EP), antiserum (10 μl) from a rabbit is incubated overnight with 10 μl of pure [$^{125}$I]Ep solution (U. of California, Berkeley). The immune complexes are precipitated by the addition of 100 μl of formalin-fixed Staphylococcus aureus (Cowan strain), 10% suspension (PanSorbin, Calbiochem). Forty percent of the radioactivity of the [$^{125}$I]Ep sample precipitates in that procedure. Polyacrylamide gel electrophoresis and subsequent autoradiography demonstrate that the radioactivity precipitated by the anti-serum corresponds to the 39,000 MW protein of [$^{125}$I]Ep. Moreover, the immunoprecipitation of [$^{125}$I]Ep by these antibodies is inhibited in a concentration-dependent fashion by crude biologically active Ep and by PP.

In a similar manner, antiserum is incubated with biologically active Ep and immuno-precipitation carried out. A bioassay of the supernatants demonstrates that over 90% of the Ep activity is precipitated by the anti-PP serum.

We turn next to a description of an immunoassay using the above-described tracer and antibody.

Immunoassay

An immunoassay for the protein may be performed by mixing a sample having an unknown concentration of protein with a known amount or concentration of the tracer, and with the antibody. Using the general formula Pr for the protein, Ab for the antibody, and Tr* for the labeled polypeptide tracer,

Pr/Ab←Pr+Ab+Tr*→Ab/Tr*

The amount of Ab/Tr* formed may be determined from radioactive measurement; from that measurement and the known initial concentration of Tr*, the initial concentration of Pr may be derived. The higher the concentration of Pr, the less Ab/Tr* formed.

The radioimmunoassay for erythropoietin is performed as follows, with dilutions being made in Dulbecco's phosphate buffered saline (PBS), 2 mg/ml BSA, 0.02% NaN$_3$. First, the following are pipetted into a series of 500 μl of polypropylene conical Eppendorf tubes:

(1) 10 μl [$^{125}$I]PP solution (10,000 cpm);

(2) (when standardizing) 10 μl human erythropoietin standard at the following concentrations (mU): 0; 0.25; 2.5; 25; 250; or 2500; alternatively (when performing an assay on a sample of unknown concentration) 10 μl of the unknown sample; and (3) 20 μl of anti-PP serum diluted 1:1000. The tubes are incubated at 4° C. for 16 hours. To each tube is added 50 μl of 10% Staphylococcus suspension (Pansorb). The tubes are then incubated at 4° C. for 1 hour, and centrifuged (5000 g) for 5 minutes. The supernatants are aspirated off, and the residue is washed with 100 μl of phosphate-buffered saline/bovine serum albumin solution. The wash of each tube is pooled with the respective tube's supernatant, and the radioactivity of each is determined. From the standards, a plot is made of [$^{125}$I]PP precipitated (% maximal) versus the log Ep concentration. The concentration of unknown Ep samples is determined by extrapolation of the percentage of [$^{125}$I]PP precipitated using the standard curve.

The immunoassay may conveniently be packaged as a kit for use, e.g., in diagnostic laboratories, by providing the labeled polypeptide antigen and the antibody in separate storage means and in quantities suitable for use with samples.

We turn next to a method of purifying a protein using the antibody described above.

Protein Purification

Antibodies raised to the antigen as described above may be used to purify the protein by immunological techniques known to those in the art, e.g., by introducing the antibody into a mixture containing the protein, separating the bound protein/antibody from the mixture, and then separating the protein from the antibody.

OTHER EMBODIMENTS

Other embodiments are within the following claims. For example, the labeling of the polypeptide tracer may be accomplished by binding it to a plastic microwell for use in an enzyme-linked immunosorbent assay (ELISA). The concentration of Ep is determined by introducing a solution of the antibody and an unknown concentration of Ep to the microwell-bound polypeptide, and, using horseradish peroxidase in a manner similar to the above description with respect to screening the antibodies for PP affinity, determining the amount of antibody bound to the polypeptide.

We claim:

1. A method of immunoassay for erythropoietin comprising
   (A) first incubating a mixture comprising
      (1) a sample having an unknown amount of erythropoietin,
      (2) an antibody raised to a polypeptide, or to said polypeptide linked to a carrier, wherein said polypeptide is an amino acid sequence of between 6 and 26 amino acids corresponding to an epitope of erythropoietin contained within the 26 N-terminal amino acids of erythropoietin, said antibody having the characteristic of separately binding both to erythropoietin and to said polypeptide, and
      (3) a tracer comprising said polypeptide linked to a label, said tracer lacking a complete erythropoietin sequence, and then,
   (B) determining the concentration of erythropoietin based on the amount of unbound tracer or tracer bound to said antibody.

2. The method of claim 1 further characterized in that said erythropoietin is human erythropoietin.

3. An antibody raised to a polypeptide or to said polypeptide linked to a carrier, wherein said polypeptide is an amino acid sequence of between 6 and 26 amino acids corresponding to an epitope of erythropoietin contained within the 26 N-terminal amino acids of erythropoietin, said antibody having the characteristic of binding separately both to erythropoietin and to said polypeptide.

4. The antibody of claim 3 further characterized in that said erythropoietin is human erythropoietin.

5. The antibody of claim 3 further characterized in that said antibody is bound to an immunoaffinity gel.

6. The antibody of claim 3 further characterized in that said antibody is bound to an immunoaffinity resin.

7. A method of making the antibody of claim 3 comprising the steps of,
   providing said polypeptide, and
   administering to a mammal said polypeptide or a carrier linked to said polypeptide.

8. The method of claim 7 further characterized in that said erythropoietin is human erythropoietin.

9. An antibody raised to a polypeptide or to said polypeptide linked to a carrier, wherein said polypeptide comprises a fragment of at least a sequence of 6 amino acids, from the following sequence: H$_2$N-ala-pro-pro-arg-leu-ile-asn-asp-ser-arg-val-leu-glu-arg-tyr-leu-leu-glu-ala-lys-glu-ala-glu-lys-ile-thr-COOH.

10. The antibody of claim 9 further characterized in that said polypeptide comprises the sequence: H$_2$N-ala-pro-pro-arg-leu-ile-asn-asp-ser-arg-val-leu-glu-arg-tyr-leu-leu-glu-ala-lys-glu-ala-glu-lys-ile-thr-COOH.

11. A method of making the antibody of claim 9 comprising the steps of
   providing said polypeptide, and
   administering to a mammal said polypeptide or a carrier linked to said polypeptide.

12. The method of claim 11 further characterized in that said polypeptide comprises the sequence: H$_2$N-ala-pro-pro-arg-leu-ile-asn-asp-ser-arg-val-leu-glu-arg-tyr-leu-leu-glu-ala-lys-glu-ala-glu-lys-ile-thr-COOH.

13. A method of immunoassay for erythropoietin comprising
   (A) first incubating a mixture comprising
      (1) a sample having an unknown amount of erythropoietin,
      (2) an antibody raised to a polypeptide, or to said polypeptide linked to a carrier, wherein said polypeptide is an amino acid sequence of between 6 and 26 amino acids corresponding to an epitope of erythropoietin contained within the 26 N-terminal amino acids of erythropoietin, said antibody having the characteristic of separately binding both to erythropoietin and to said polypeptide, and
      (3) a tracer comprising an amino acid sequence of between 6 and 26 amino acids corresponding to an epitope of erythropoietin contained within the 26 N-terminal amino acids of erythropoietin, said sequence being linked to a label, said tracer lacking a complete erythropoietin sequence, and then,
   (B) determining the concentration of erythropoietin based on the amount of unbound tracer or tracer bound to said antibody.

14. A kit for performing the immunoassay of claim 13 comprising
   a supply of said antibody,
   a supply of said tracer,
   means to store said tracer supply, and
   means to store said antibody supply.

15. The kit of claim 14 further characterized in that said polypeptide comprises the sequence: H$_2$N-ala-pro-pro-arg-leu-ile-asn-asp-ser-arg-val-leu-glu-arg-tyr-leu-leu-glu-ala-lys-glu-ala-glu-lys-ile-thr-COOH.

* * * * *

Notice of Adverse Decisions in Interference

In Interference No. 102,378, involving Patent No. 4,590,168, A. J. Sytkowski, and J. M. Sue, PROTEIN IMMUNOASSYING AND PURIFICATION, final judgment adverse to the patentees was rendered July 17, 1991, as to claims 1-15.

*(Official Gazette August 27, 1991)*